United States Patent [19]

Minka

[11] 4,022,229
[45] May 10, 1977

[54] DENTAL FLOSS HOLDER

[76] Inventor: Karlis Minka, 204 E. Joppa Road, Towson, Md. 21204

[22] Filed: Aug. 5, 1976

[21] Appl. No.: 711,722

[52] U.S. Cl. .............................................. 132/92 R
[51] Int. Cl.² ....................................... A61C 15/00
[58] Field of Search ..................... 132/92 R, 91, 90

[56] References Cited

UNITED STATES PATENTS

| 2,052,520 | 8/1936 | Sonnenberg | 132/92 R |
| 2,516,539 | 7/1950 | Atols | 132/92 R |
| 2,644,469 | 7/1953 | Cohen | 132/92 R |
| 2,756,758 | 7/1956 | Segerblom | 132/92 R |
| 3,913,597 | 10/1975 | Day | 132/92 R |

*Primary Examiner*—G.E. McNeill

[57] ABSTRACT

A hollow handle adapted to receive a supply of dental floss. A cap in releasable assembly with the handle. The cap comprises studs for supporting a length of floss which is pulled from the supply. The assembled cap and handle form a clamping engagement and a V-shaped groove between the same two surfaces for locking the floss so that it is held taut between the studs during flossing. The cap has a male shank for assembly with a female engaging end of the handle.

11 Claims, 2 Drawing Figures

DENTAL FLOSS HOLDER

BACKGROUND OF THE INVENTION

This invention relates to dental floss holders of the type having a hollow handle and a cap in releasable assembly with the handle, the cap having a pair of studs for supporting a portion of a length of floss which is used for flossing teeth, the assembly providing a clamping and a wedging arrangement to lock respectively the beginning and the end of the length of floss. Prior art often involves rigorous manufacturing requirements for such holders.

SUMMARY OF THE INVENTION

This invention is an improvement of such holders in the sense that the use of the same two surfaces, namely, a bottom surface on the cap and an end surface on the handle, to perform both the clamping and the wedging functions of the holder in combination with a male shank on the cap and a female engaging end on the handle for a releasable assembly of the holder results in either simplified manufacturing methods or substantially reduced dimensional tolerance requirements for the finished parts. Because the clamping and the wedging elements of the holder are embodied in the same two surfaces, there are no close tolerance or elasticity requirements between the elements as there would be if the elements were disposed in two distinct pairs of surfaces.

The invention further includes in combination with the bottom surface and the end surface various other features to facilitate the use of the holder. Such other features and advantages of the invention will be apparent from the following description and claims with reference to the accompanying drawing.

DESCRIPTION OF THE PREFERRED EMBODIMENTS

Figure 1:
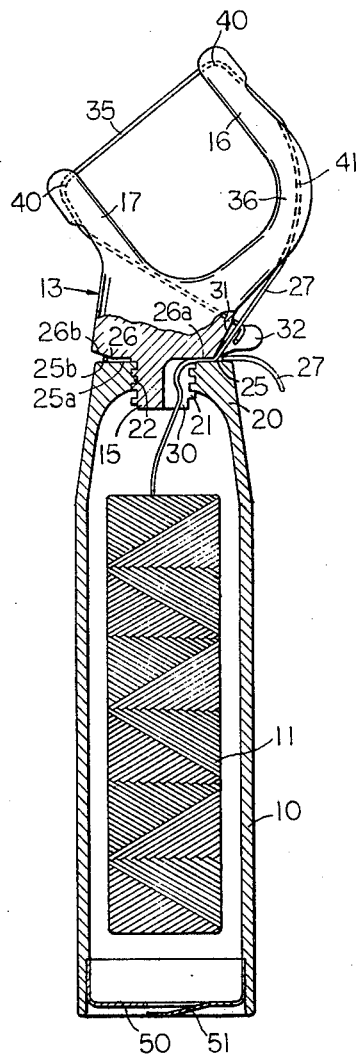
FIG. 1 is a view in elevation of the holder in partial cross section showing the cap and handle assembly with a supply of floss inside the handle.

In FIG. 1, the hollow handle 10 is shown with a supply of floss 11 inside the handle. The cap 13, shown assembled with the handle, has a shank 15 and spaced apart studs 16 and 17 integral with the cap. The shank 15 is releasably assembled with the engaging end 20 of the handle, the shank and the engaging end constituting a male and a female element, respectively; and both the male shank and the female engaging end having square threads 21 and 22, respectively.

The handle 10 has an annular continuous end surface 25 on the engaging end 20 and the cap 13 has an annular continuous bottom surface 26 at the root of the shank 15, both surfaces extending transversely outwardly with respect to the longitudinal axis of the holder and facing one another in the assembled condition. The bottom surface 26 has an annular inward portion 26a and an annular outward portion 26b, the portions being inclined in cross section with respect to one another. The end surface 25 is preferably flat and it also has an annular inward portion 25a and an annular outward portion 25b, both portions being determined by the respective portions of the bottom surface 26. The inward portions 26a and 25a are substantially parallel to one another with the beginning of a length of floss 27 clamped therebetween and the outward portions 26b and 25b forming an annular outwardly facing V-shaped groove. The thus formed V-shaped groove has a width of dimensions sufficient for inward wedging of the end of the length of floss into the groove.

The cross section of both the end surface 25 and the bottom surface 26 is not limited to the illustration shown in the drawing as obvious variations may be employed, for example, one or both of the surfaces may be curved in cross section converging inwardly. The outside diameter of the bottom surface 26 is preferably slightly larger than the outside diameter of the end surface 25 to aid in entrance of the floss into the V-shaped groove. The square threads 21 and 22 on the male shank 15 and on the female engaging end 20 may be replaced by other means of engagement, for example, regular V-shaped threads. However, the square threads are preferred because they permit the formation of an annularly uniform V-shaped groove.

Figure 2:
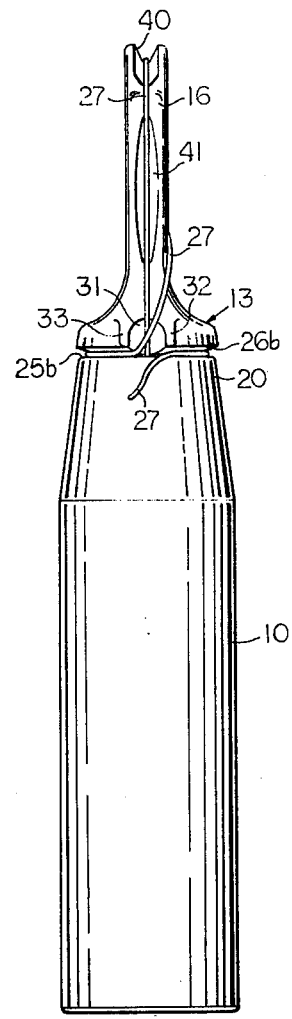
FIG. 2 is a side view of the holder shown in FIG. 1.

The shank 15 has a passageway in the form of a radial slot 30 to permit a length of floss 27 to pass from the inside of the handle 10 to the outside of the holder. The slot 30 adjoins the inward portion 26a of the bottom surface, however, it may be slightly offset with respect to the inward portion for manufacturing reasons. A recess 31 in the outward portion 26b of the bottom surface is located in line with the slot 30 to guide the emerging length of floss. Lips 32 and 33 are extending outwardly on the cap and adjoining the bottom surface 26 on each side of the recess 31 primarily to aid in guiding the end of a length of floss into the V-shaped groove. The studs 16 and 17 are slanted with respect to the longitudinal axis, stud 16 being directed toward stud 17 by the use of a bend 36 to create a suitable gap between the studs. The studs 16 and 17 are also disposed to slant the portion 35 of a length of floss with respect to the longitudinal axis permitting a better access to the back teeth of both sides of the mouth for a person who is either right or left handed. Slot 30, recess 31, lips 32 and 33, and studs 16 and 17 are all located in line for placing and guiding a length of floss on the holder as best seen in FIG. 2. The recess and one or both of the lips may be eliminated if desired, however, they are preferred because of a better control of the floss afforded thereby.

Floss supporting means in the form of a supporting groove 40 is located on the top end of each of the studs 16 and 17 for retaining the portion 35 of the length of floss therebetween. A second supporting groove 41 is located on the outside of the bend 36 of stud 16. The floss supporting means may be in the form of other embodiments, such as holes in the studs, however, the supporting groove 40 is preferred because of easier handling of the floss and for hygienic reasons.

A metal insert 50 is pressed into the bottom end of handle 10 after a supply of floss 11 has been placed inside the handle with a length of floss 27 remaining outside the female engaging end 20. The insert 50 is provided with a floss cutter 51 which is protruding longitudinally outwardly from the insert while remaining recessed in the bottom end of the handle for reasons of safety. The holder can be made from any suitable material, such as a suitable plastic.

To operate the holder, the cap 13 is screwed tight into the engaging end 20 with the floss passing through the radial slot 30 and the beginning of the length of floss clamped between the inward portions 25a and 26a of the end surface and the bottom surface, respectively. The floss is then placed in the groove 41 while being guided by recess 31 and lips 32 and 33. After the floss is placed in groove 40 on both studs 16 and 17, the end of the length of floss is pulled across to the opposite side of the cap, guided between the lips 32 and 33 and then wedged once around in the annular V-shaped groove.

After use, the cap may be unscrewed partly whereby the floss is released from engagement between the end surface 25 and the bottom surface 26, a new length of floss may be pulled from the handle and the used floss may be cut off by the cutter 51.

The form and disposition of the elements to carry out the invention is not necessarily restricted to the embodiments described herein or illustrated in the drawing. It will be understood that other modifications may be made within the spirit of the invention It is intended that no limitations be placed on the invention except as defined by the scope of the following claims.

I claim:

1. A dental floss holder having a longitudinal axis and comprising a hollow handle adapted to receive a supply of floss, said handle having an engaging end, a cap having a shank in releasable assembly with said engaging end, a passageway to permit a length of floss to pass from the inside of the handle to the outside of the holder, and spaced apart studs on said cap, the studs having floss supporting means for retaining a portion of said length of floss therebetween, wherein the improvement comprises a continuous end surface on said engaging end and a continuous bottom surface on said cap, said end surface and said bottom surface extending transversely outwardly with respect to said axis, the inward portion of said end surface and of said bottom surface cooperating to clamp the beginning of said length of floss therebetween, and the outward portion of said end surface and of said bottom surface forming an annular outwardly facing V-shaped groove therebetween, the width of said V-shaped groove being of dimensions sufficient for inward wedging of the end said length of floss into the V-shaped groove, said shank and said engaging end constituting a male and a female element, respectively.

2. A holder as in claim 1, wherein said cap has a recess in said outward portion of the bottom surface for guiding said length of floss.

3. A holder as in claim 2, wherein said shank has a slot therein to provide said passageway, said slot being located in line with said recess.

4. A holder as in claim 3, wherein said cap has an outwardly extending lip on one side of said recess, said lip adjoining said bottom surface for guiding said length of floss.

5. A holder as in claim 1, wherein said shank and said engaging end has square threads for releasable assembly to one another.

6. A holder as in claim 1, wherein the outside diameter of said bottom surface is larger than the outside diameter of said end surface.

7. A holder as in claim 1, wherein at least one of said studs is slanted with respect to said axis, one of said studs having a bend toward the other of said studs, said studs being disposed to slant said portion of the length of floss with respect to said axis upon placement of same on said floss supporting means.

8. A holder as in claim 7, wherein said floss supporting means comprises a supporting groove on the top end of at least one of said studs.

9. A holder as in claim 8, wherein a second supporting groove is located on the outside of said bend for placing the floss thereon.

10. A holder as in claim 1, wherein said handle has a cutter on the bottom end thereof for cutting off used floss.

11. A holder as in claim 1, wherein said handle includes said supply of floss to provide said length of floss.

* * * * *